United States Patent [19]

Sears et al.

[11] Patent Number: 4,559,594
[45] Date of Patent: Dec. 17, 1985

[54] ELECTROSTATIC AIR CLEANER AND HIGH VOLTAGE POWER SOURCE THEREFOR

[75] Inventors: Lawrence M. Sears, Shaker Heights; Terrance C. Slaby, North Royalton, both of Ohio

[73] Assignee: Adams Manufacturing Company, Cleveland, Ohio

[21] Appl. No.: 554,928

[22] Filed: Nov. 25, 1983

[51] Int. Cl.[4] .......................... H02M 7/06; B03C 3/02
[52] U.S. Cl. ...................................... 363/126; 363/21; 55/139
[58] Field of Search ...................... 363/20, 21, 97, 131, 363/126; 323/903; 55/105, 137, 139; 307/43, 85, 86

[56] References Cited

U.S. PATENT DOCUMENTS

| 3,140,935 | 4/1964 | Flagg . | |
| 3,266,481 | 8/1966 | Wentling et al. | 126/113 |
| 3,622,839 | 11/1971 | Abrams et al. . | |
| 3,774,588 | 11/1973 | Yeagle | 126/113 |
| 3,849,670 | 11/1974 | Lourigan . | |
| 3,877,896 | 4/1975 | Muskovac . | |
| 4,052,177 | 10/1977 | Kide . | |
| 4,138,233 | 2/1979 | Masuda . | |
| 4,238,810 | 12/1980 | Stevenson et al. . | |
| 4,335,414 | 6/1982 | Weber | 363/21 |
| 4,351,648 | 9/1982 | Penney | 55/137 |
| 4,374,355 | 2/1983 | Steigerwald et al. | 363/21 |
| 4,380,044 | 4/1983 | Parr | 363/56 |
| 4,410,934 | 10/1983 | Fathauer et al. | 323/903 |
| 4,459,651 | 7/1984 | Fenter | 363/49 |

OTHER PUBLICATIONS

Honeywell Brochures, #70-9719 and 70-9302.
Trion Brochure.

*Primary Examiner*—Peter S. Wong
*Assistant Examiner*—Judson H. Jones
*Attorney, Agent, or Firm*—Yount & Tarolli

[57] ABSTRACT

Electrostatic air cleaner apparatus is disclosed for use in conjunction with existing space conditioning apparatus which includes a transformer providing a low voltage (typically 24VAC) power signal. The apparatus includes a power supply which is adapted to be coupled to the output of the transformer for providing a low voltage DC power signal. A high voltage generator and regulator is included which is powered by the low voltage DC power signal. The generator and regulator includes a flyback transformer arrangement which generates a high voltage DC signal suitable for energizing the collector and ionizer stages of an air cleaner assembly. The generator and regulator also includes closed loop feedback for regulating the amplitude of the high voltage DC signal so that it remains at or near the optimum amplitude regardless of variations in the amplitude of the low voltage power signal supplied by the existing low voltage transformer. The apparatus also includes an air cleaner assembly to which the high voltage DC signal is applied.

21 Claims, 7 Drawing Figures

ELECTROSTATIC AIR CLEANER AND HIGH VOLTAGE POWER SOURCE THEREFOR

BACKGROUND AND FIELD OF THE INVENTION

The present invention relates to an electrostatic air cleaner, and more particularly to an electrostatic air cleaner which can be powered from a low voltage transformer normally associated with other space conditioning apparatus.

As used, in this application, the term "space conditioning apparatus" will be understood to refer to air conditioning equipment, furnaces and other heating equipment, air humidifying equipment, and any and all other apparatus for conditioning the air in a residential, commercial, or industrial establishment.

Electrostatic air cleaners have long been used for removing particulate matter such as dust and pollen from the air as it passes through a furnace, air conditioner, or other space conditioning apparatus. Occasionally, the electrostatic air cleaner is installed at the same time that the furnace or air conditioner is initially installed. Often, however, less expensive fiberglass filters are initially used with the furnace, the electrostatic air cleaner being added only later.

When an electrostatic air cleaner is retrofitted to an existing furnace, one of the problems encountered is the availability of line voltage power to operate the electrostatic air cleaner. There may not be a convenient power outlet in the vicinity of the furnace. Thus, the person installing the electrostatic air cleaner may be forced to run an electrical line specifically for the air cleaner. Furthermore, most building codes require that line voltage power cables for permanently installed equipment be run in conduit or otherwise armored. This makes it both more difficult and more expensive for a homeowner to install an electrostatic air cleaner.

SUMMARY OF THE INVENTION

Most existing space conditioning apparatus include a 24 volt transformer for supplying power to relays, thermostats, etc. The 24 volt transformer provides a ready existing source of power which could be used to power ancillary equipment. The 24 volt power is also easier to hook up to than 110 volt power. There is less danger of electrocution and, also, building codes do not require that 24 volt lines be armored or run in conduit. The ancillary equipment, however, must be specifically designed to operate from a 24 volt power line. Unfortunately, conventional electrostatic air cleaners do not fit into this category.

Known electrostatic air cleaners are designed to be powered from 110 volt outlets, and generate the high voltage needed to operate the air cleaner by directly multiplying the line voltage with a high voltage transformer and rectifier arrangement. The high voltage thus produced is relatively stable since the line voltage is, itself, relatively stable. A similar approach cannot be used in conjunction with the 24 volt supply provided by the existing 24 volt transformer, however. The 24 volt signal provided by the transformer varies substantially in amplitude under normal operating conditions and thus, if merely multiplied, would produce a high voltage which varied in similar fashion. The efficiency of operation of an electrostatic air cleaner is very sensitive to the magnitude of the high voltage signal. Thus, average efficiency would be impaired if the high voltage did not remain near its optimum level.

Moreover, the 24 volt transformer utilized in existing space conditioning apparatus has a limited capacity, and therefore cannot be used to provide power to circuitry whose current demands are excessive.

The present invention is directed to electrostatic air cleaner apparatus, adapted for use in conjunction with space conditioning apparatus having a transformer for providing a low voltage AC power signal. An apparatus constructed in accordance with the present invention includes a power supply unit for converting the low voltage AC signal to a low voltage DC power signal. A high voltage generator and regulator is powered by the low voltage DC for generating a high voltage DC signal suitable for energizing the collector plates of an electrostatic air cleaner and for regulating said high voltage DC signal so that it remains within a selected range of voltages. The apparatus also includes an assembly of plural collector plates arranged to permit air to pass through them, and means for coupling the high voltage DC signal generated by the high voltage generator and regulator across the plates of the collector plate assembly.

The apparatus is thus capable of being directly connected to the low voltage AC output provided by an existing low voltage AC transformer, whereby it can be installed by a typical homeowner or contractor without the necessity of running additional power lines to the space conditioning apparatus. The high voltage generator apparatus used in the electrostatic air cleaner includes elements for regulating the high voltage DC signal such that it maintains the high voltage signal within a suitable range regardless of variations in the amplitude of the low voltage AC signal provided by the existing transformer. Moreover, the high voltage generator and regulator circuit draws relatively little current, whereby it does not excessively load the output of the existing transformer.

BRIEF DESCRIPTION OF THE DRAWINGS

The foregoing and other objects and advantages of the present invention will become more readily apparent from the following detailed description, as taken in conjunction with the accompanying drawings, wherein.

DETAILED DESCRIPTION

Figure 1:
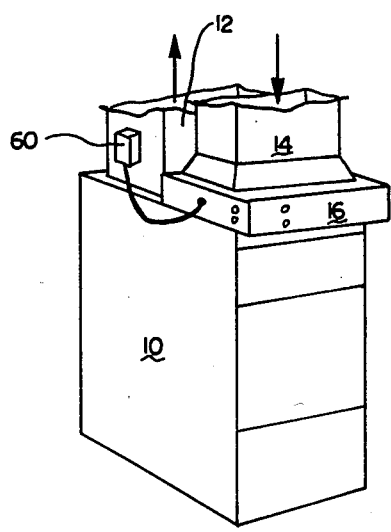
FIG. 1 is a perspective drawing of a space conditioning apparatus including an electrostatic air cleaner in accordance with the teachings of the present invention.

FIG. 1 illustrates a conventional placement of an electrostatic air cleaner in existing space conditioning apparatus. In FIG. 1, the space conditioning apparatus takes the form of a furnace 10 for a forced air heating system. The furnace 10 is connected to the heating system by an outlet air duct 12 and a return air duct 14. The electrostatic air cleaner 16 is normally installed between the return air duct 14 and the furnace 10.

Figure 2:
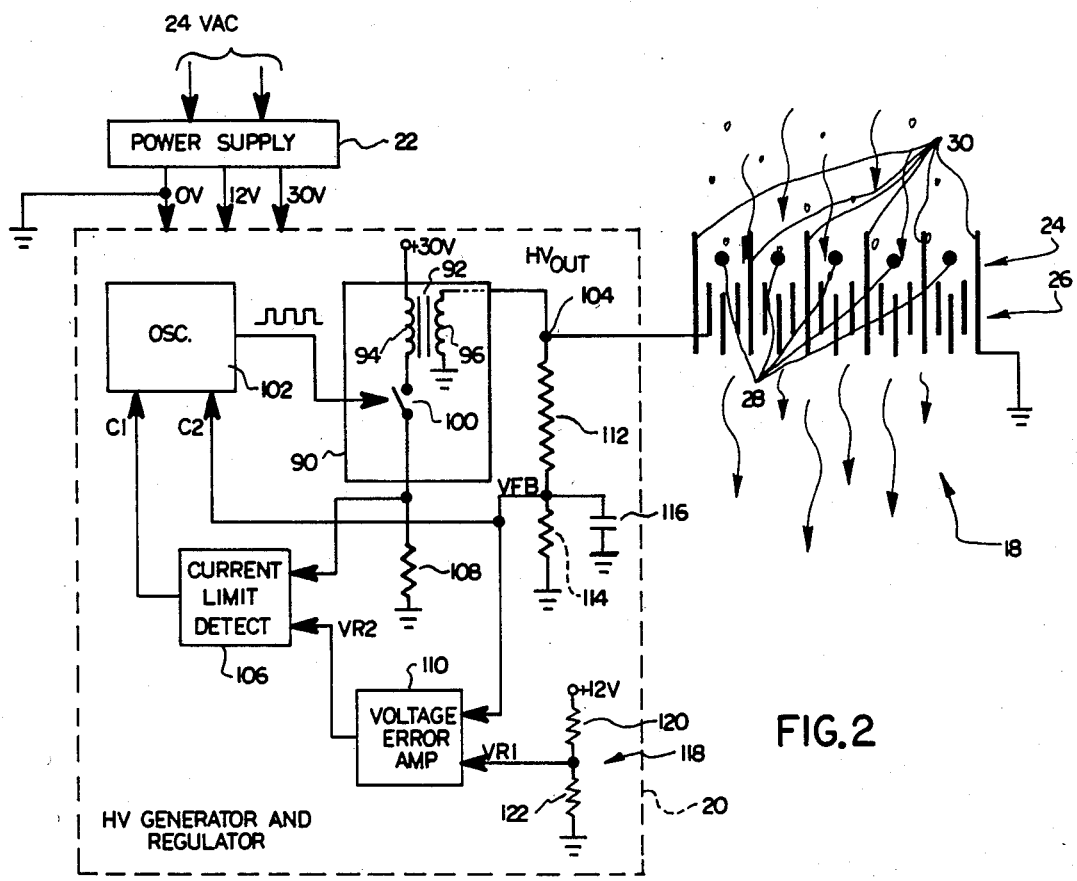
FIG. 2 is a block diagram of the high voltage generator and regulator circuit for the air cleaner, in association with the ionizer and collector stages of the electrostatic air cleaner of FIG. 1.

As shown in FIG. 2, the electrostatic air cleaner 16 includes a two-stage air flow section 18, a circuit 20 for generating and regulating the high voltage DC signal which is applied to the air flow section 18, and a power supply circuit 22 for supplying low voltage DC power to the high voltage generator and regulator 20. The power supply 22 is designed to be operated from the low voltage AC power signal generated by an existing 24 V transformer.

The two-stage air flow assembly 18 includes an ionizer stage 24 and a collector stage 26. The ionizer stage 24 includes a plurality of parallel corona discharge wires 28 disposed in a common plane essentially perpendicular to the direction of air flow, where the corona discharge wires 28 are separated by ground plates 30. The ground plates 30 run parallel to the corona discharge wires 28, and are each disposed midway between a corresponding pair of corona discharge wires.

A high voltage DC electrical signal is applied to the corona discharge wires by the high voltage generator and regulator 20, thereby establishing a high intensity electrostatic field around each corona discharge wire. The electrostatic field in turn produces a corona between the wires and the plates which electrically charges the particulate matter passing between the wires and the plates.

Figure 3:
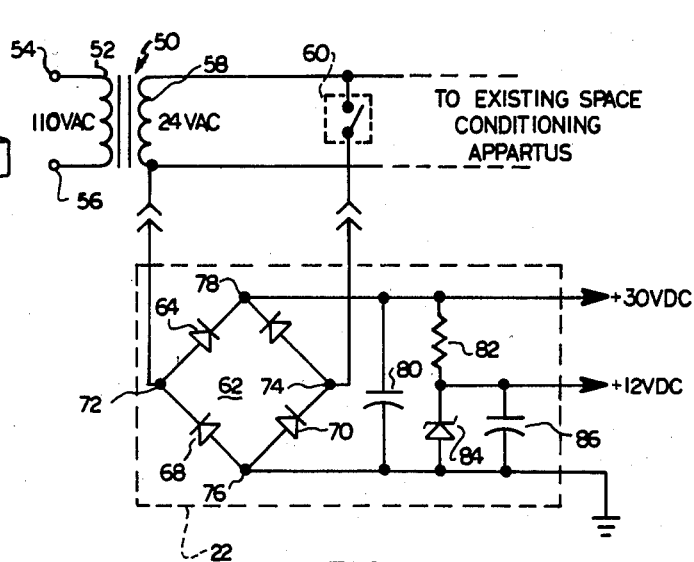
FIG. 3 is a circuit schematic showing the power supply unit of the electrostatic air cleaner and the manner in which it is connected to the low voltage AC transformer of existing space conditioning apparatus.

The collector stage 26 of the air flow assembly 18 is located immediately beneath the ionizer stage and is disposed parallel to it. The collector stage is comprised of plural closely spaced, parallel plates, forming a generally grill-like arrangement. The plate on the far left, as viewed in FIG. 3, is connected to electrical ground, and thereafter every alternate plate of the collector section is similarly grounded. The remaining plates, in other words those disposed midway between the ground plates, are all connected to the high voltage output of the high voltage generator and regulator 20. Thus, a high voltage electrostatic field is also formed between the plates of the collector section 26. In the embodiment illustrated in FIG. 2, the ground plates of the ionizer stage are actually ground plates from the collector stage which have been extended to reach between the corona discharge wires. Every other ground plate is thus extended, hence there are only approximately half as many ground plates in the ionizer stage as in the collector stage.

The air cleaner is installed between the return air duct 14 and the inlet opening of the furnace 10 with the ionizer stage 24 located upstream of the collector stage 26. Consequently, the air first flows through the ionizer stage, and then through the collector stage. Upon passing through the ionizing grid, the particulate matter acquires an electrical charge. Thus, when the air thereafter flows through the electrostatic field established between adjacent plates of the collector stage 26, the particulate matter is attracted to one or the other of the nearest two adjacent plates. The particulate matter is therefore deflected towards one of the collector plates and eventually strikes and sticks to the collector plate, being thereby removed from the air flow.

In order for the two stages of the electrostatic air cleaner to operate properly, a high voltage DC signal must be supplied to them. Conventionally, the high voltage DC signal is generated by a power supply including a transformer powered from a conventional 110 volt AC line. The transformer boosts the voltage to a point at which it can be rectified and directly used by the ionizer and collector stages of the air cleaner.

In accordance with the present invention, however, the high voltage DC signal is instead generated by a high voltage generator and regulator circuit 20, powered by a power supply 22. The power supply 22 is operated from a 24 volt transformer already present in the existing space conditioning apparatus.

In FIG. 3, the 24 volt AC transformer conventionally found in furnaces, air conditioners, etc. is indicated at 50. The primary winding 52 of the transformer includes two terminals 54 and 56 which are conventionally connected to an existing 110 volt AC line. The secondary winding of the transformer carries a 24 volt AC signal, and is connected to conventional thermostats, relays, etc. associated with the furnace 10 or other existing space conditioning apparatus. The power supply 22 of the electrostatic air cleaner is designed to derive its power from the secondary winding 58 of the transformer 50.

The power supply 22 is connected across the secondary winding 58 in series with a control switch, such as sail switch 60. The sail switch 60 is a single pole, single throw switch having a toggle arm which can be operated with a minimum of applied force. The toggle arm of the sail switch is connected to a sail. The sail switch 60 is adapted to be mounted on the side of the furnace such that its sail is in the path of air flow in the outlet air duct 12 (see FIG. 1). When the fan associated with the furnace 10 is turned off, the sail will hang down within the outlet air duct 12, placing the sail switch 60 in an "open" state. When the fan associated with the furnace 10 turns on, however, air flow forces the sail to a position wherein the sail switch 60 is closed. Thus, the circuit between the secondary winding 58 of the transformer and the power supply 22 is only completed when the furnace fan is operating.

It will be noted that the wires connecting the air cleaner to the transformer and sail switch carry only low voltage AC. This is advantageous for several reasons. It reduces the danger that the individual installing the air cleaner will suffer a harmful electrical shock. Also, it means that unarmored electrical cables can be used, thereby reducing the cost and difficulty of installing the air cleaner.

The power supply 22 includes a conventional full wave rectifier 62 including four diodes 64, 66, 68, 70. The AC input terminals 72 and 74 of the full wave rectifier are connected to the input terminals of the power supply 22, and thus receive 24 volts AC when the sail switch 60 is closed. Full wave rectifier 62 rectifies the 24 volt AC signal to thereby generate a 30 volt DC signal across the output terminals 76 and 78 of the transformer. The 30 volt DC signal is filtered by a capacitor 80 connected across the output terminals 76 and 78 of the full wave rectifier. The negative output terminal 76 of the full wave rectifier is connected to the ground reference point of the apparatus.

A resistor 82 and zener diode 84 are connected in series across the output terminals 76 and 78 of the full wave rectifier. The zener diode 84 has a zener voltage of 12 volts, whereby it maintains a 12 volt drop across it as long as some current is passing through it. Resistor 82 is selected so that an adequate level of current passes through the zener diode 84 to maintain regulation under all conditions. A capacitor 86 is connected across the zener diode to further smooth and filter the 12 volt power signal appearing across the zener diode. The 30 volt DC signal across the full wave rectifier 62 and the 12 volt DC signal across the zener diode 84 power the high voltage generator and regulator circuit 20 in FIG. 2.

The general operation of the high voltage generator and regulator can be understood through reference to the block diagram of FIG. 2. The heart of the high voltage generator and regulator is a high voltage flyback circuit 90. The flyback circuit 90 includes a flyback transformer 92 having primary and secondary windings 94 and 96. The primary winding 94 is connected across the +30 V DC supply in series with a switching circuit, schematically represented as a switch 100 in FIG. 2, and a current sensing resistor 108. The switch 100 is periodically opened and closed to generate the high voltage signal. When the switch 100 is closed, current flows through the primary winding 94, causing a magnetic field to build up in the transformer 90. When the switch 100 thereafter opens, current through the primary winding is interrupted, causing the magnetic field to abruptly collapse. Each abrupt collapse of the magnetic field induces a high amplitude voltage spike across the secondary winding 96. The inductive spikes are rectified and filtered by a circuit not shown in FIG. 2, thus providing the high voltage DC signal needed by the air cleaner. The high voltage DC signal appears on an output terminal 104.

The switch 100 is normally open, but closes in response to pulses provided to it by an oscillator 102. The duration of the pulses is controlled by a current limit detector circuit 106. The current limit detector 106 compares the voltage appearing across current sensing resistor 108 (which is directly proportional to the level of current passing through the primary winding of the flyback transformer) with a reference voltage VR2 provided by a voltage error amplifier 110. The output of the current limit detector is at a low voltage level (approximately ground potential) as long as the current through the primary winding 94 of transformer 92 is below the reference level represented by reference voltage VR2. The current through the winding 94 is essentially zero during the intervals between the pulses provided by oscillator 102, hence the output of the current limit detector 106 will certainly be low during those intervals. The current through the primary winding 94 increases almost linearly during each pulse, however. At some point during each pulse, the voltage across current sensing resistor 108 will rise above the reference level (VR2), at which point the output of the current limit detector 106 will shift high (approximately 12 volts). The high signal appearing at the output terminal C1 of the current limit detector 106 causes the oscillator 102 to terminate the output pulse, thus opening the switch 100 and interrupting the current passing through the primary winding 94.

The high voltage developed across the secondary winding of the flyback transformer is directly related to the magnitude of the current flowing through the primary of the flyback transformer at the time that current is interrupted. In the embodiment being described, the magnitude of the flyback voltage (and thus the high voltage DC at the output of the generator and regulator 20) is adjusted by regulating the current level at which the switch is opened.

The switching point of switch 100 is adjusted by adjusting the reference voltage VR2. The reference voltage is supplied by a voltage error amplifier 110, and is increased or decreased in accordance with the difference between the desired and actual value of the high voltage DC signal appearing at the output terminal 104 of the high voltage flyback circuit 90. The actual voltage appearing at the output terminal 104 is measured by a resistive voltage divider including a large number of series-connected resistors (indicated collectively at 112) and resistor 114. A plurality of resistances are used at 112 in order to reduce the magnitude of the voltage drop appearing across any one of the resistors, whereby arcing across the resistors is avoided.

A capacitor 116 is connected between the junction of resistors 112 and 114 and ground to filter the DC signal appearing at the junction. The voltage at the junction between the resistances 112 and 114 is directly related to the high voltage DC signal at the output terminal 104, but is smaller by a factor related to the ratio of resistors 112 and 114.

The voltage error amplifier 110 compares the divided down voltage with a reference voltage VR1 provided by a voltage divider 118. The voltage divider 118 is comprised of two resistors 120 and 122 connected in series between the +12 volt supply line and ground. The ratio of the resistors 120 and 122 is selected such that a voltage VR1 is developed which is equal to the voltage (VFB) which will appear at the junction between resistances 112 and 114 when the high voltage DC output signal has the correct value (in other words, approximately 6700 volts).

If the feedback voltage VFB at the junction between resistors 112 and 114 is greater than the reference value VR1, the output of voltage error amplifier 110 will diminish somewhat, thereby reducing the maximum current which can pass through the flyback transformer 94 before the switch 100 is opened. This, in turn, has the effect of reducing the magnitude of the flyback voltage generated across the secondary of the flyback transformer.

If, on the other hand, the feedback voltage VFB is lower than the reference voltage VR1, the reference voltage VR2 applied to the current limit detector by the voltage error amplifier will increase somewhat, thereby enabling the current through the flyback transformer to rise to a slighly greater level before switching occurs. Thus, the flyback voltage will increase somewhat, thereby increasing the feedback voltage VFB back to the reference voltage VR1. The high voltage DC output of the circuit 20 is automatically regulated by this closed loop voltage regulation process.

The voltage regulation circuitry described above is capable of maintaining the output voltage at the desired 6700 volt level under normal conditions. If a piece of debris lodges between the plates of the collector, however, the output terminal 104 of the high voltage generator and regulator circuit will be essentially connected to ground, whereby the high voltage regulator will be unable to maintain the output voltage at the correct value. Furthermore, in the process of trying to reestablish the correct high voltage value, the circuit will tend to draw excessive current. To prevent this, a second control line C2 is provided to the oscillator 102. The feedback voltage VFB is applied directly to the control terminal C2. The oscillator is sensitive to the voltage on the control line C2 in the following manner. As long as the feedback voltage VFB is approximately equal to the reference voltage VR1, the oscillator operation is unaffected and high voltage regulation takes place as described above. If the voltage VFB drops percipitously, on the other hand, the oscillator 102 responds by operating at a much lower frequency, thereby limiting the maximum current which can be supplied to the output terminal 104. The current limit detector and voltage error amplifier operate as before, only now the current through the primary winding 94 of the transformer may not rise above the level represented by reference voltage VR2, due to an automatic limit on maximum pulse duration built into the oscillator 102.

Figure 4:
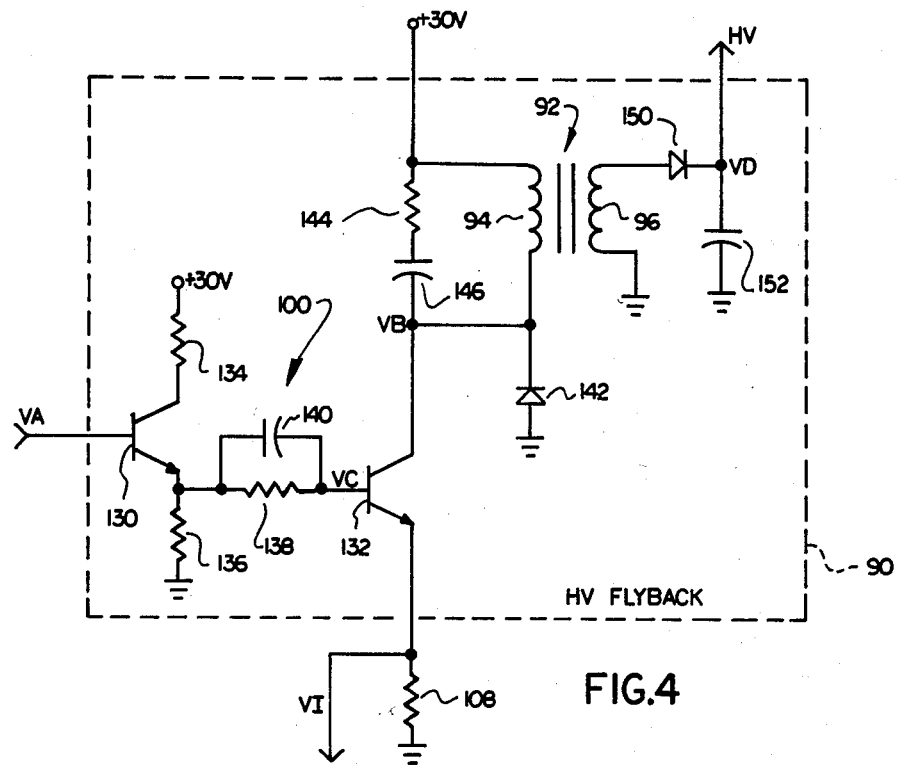
FIG. 4 is a circuit schematic of the high voltage flyback transformer circuit which is used in the high voltage generator and regulator circuit of FIG. 2 to generate the high voltage signal.
Figure 5:
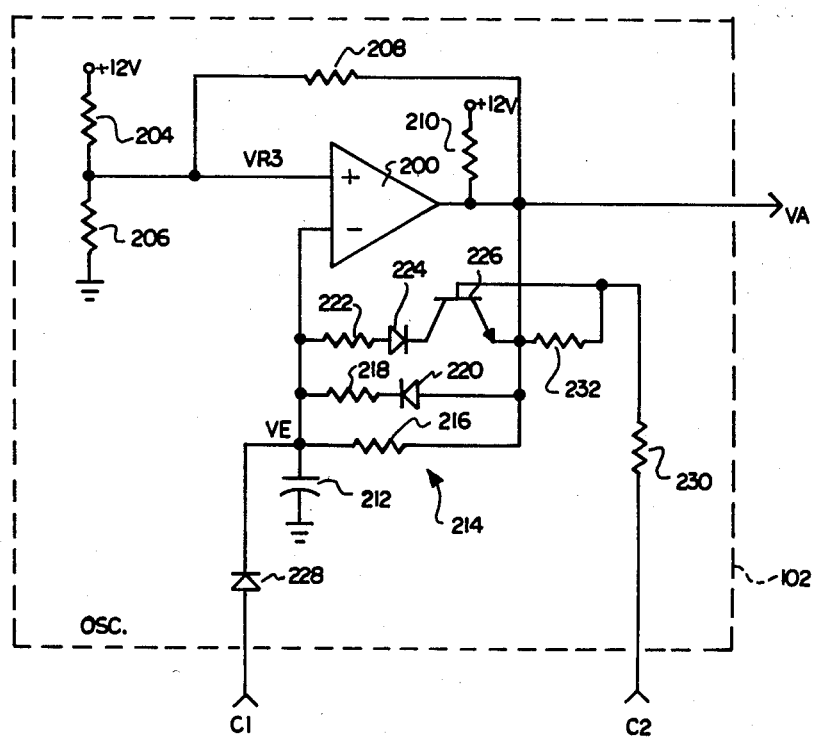
FIG. 5 is a circuit schematic of the oscillator which provides a pulse signal to the flyback transformer circuit of FIG. 4.
Figure 6:
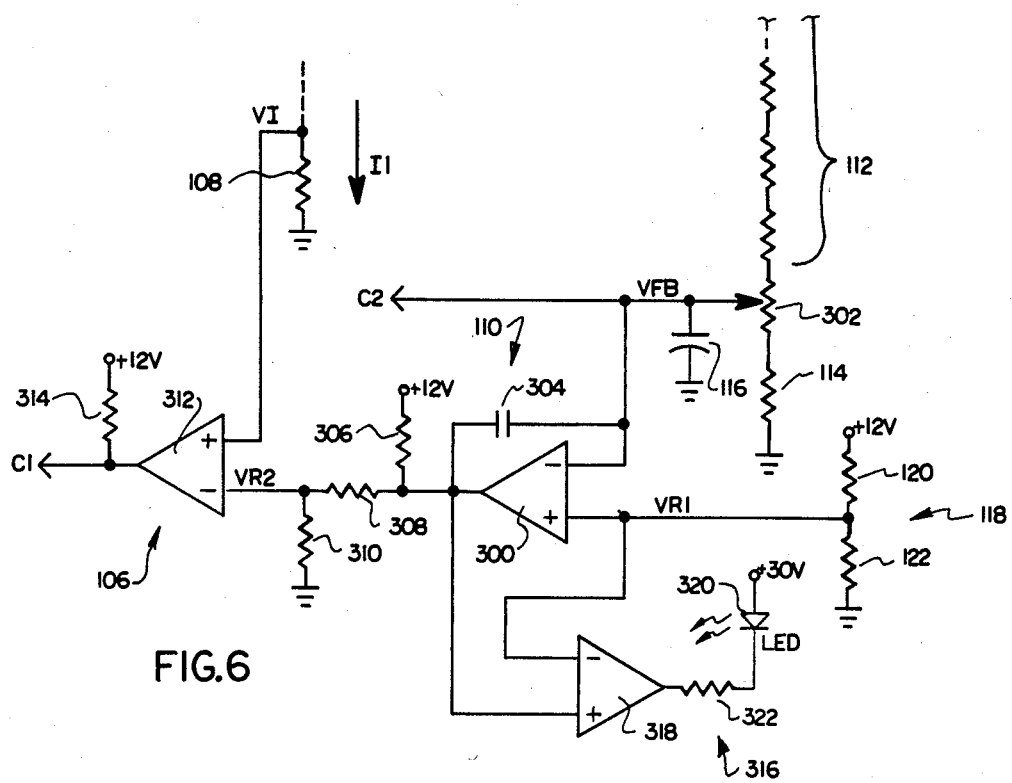
FIG. 6 is a circuit schematic of the current limit detector and voltage error amplifier blocks of FIG. 3.
Figure 7:
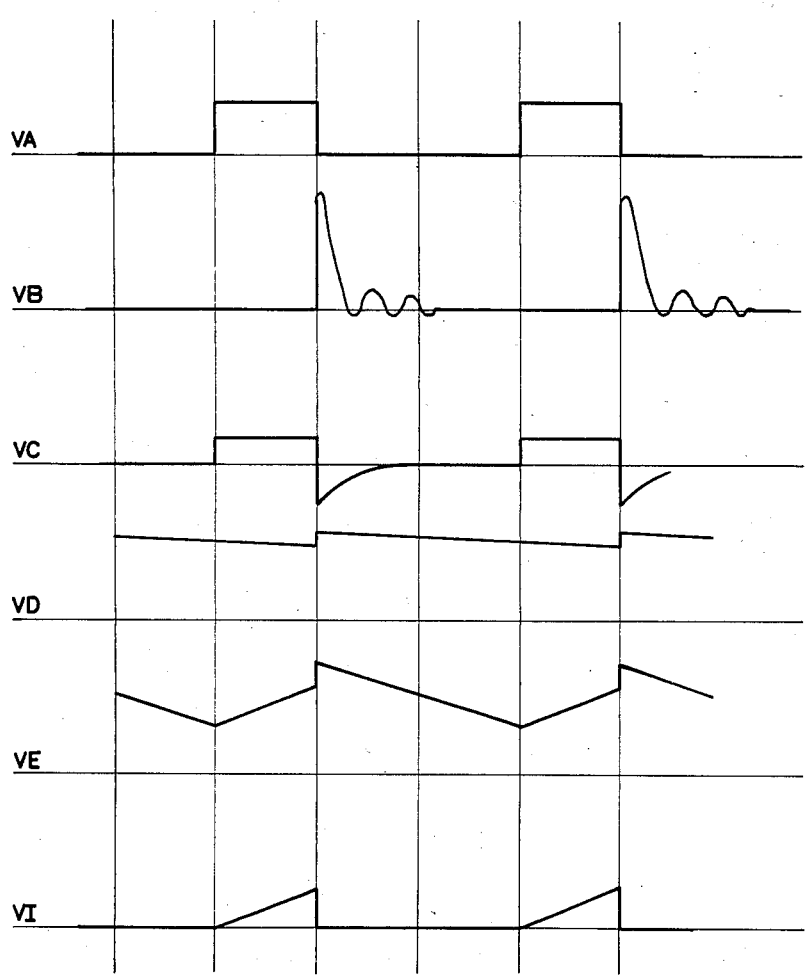
FIG. 7 is a series of diagrams showing voltage waveforms at several places in the circuitry of FIGS. 4 and 5.

FIGS. 4, 5 and 6 are more detailed circuit schematics of one embodiment of the various sections of the high voltage generator and regulator of FIG. 2. In reviewing the descriptions which follow, reference should be had to the waveforms of FIG. 7. The illustrated waveforms correspond to waveforms which appear at various places throughout the circuitry of FIGS. 4, 5 and 6. More specifically, the waveforms VA, VB, VC, and VD are waveforms found at various places in the high voltage flyback circuit 90 of FIG. 4, and the waveforms VA and VE are found in the oscillator circuit 102 of FIG. 5.

FIG. 4 is a circuit schematic of one embodiment of the high voltage flyback circuit 90. As shown in FIG. 4, the switching circuit 100 comprises a solid state switch including two cascaded NPN transistors 130 and 132. Transistor 132 has its collector-emitter current path connected in series with the primary winding 94 of the high voltage transformer, and accomplishes the actual switching of the current through the primary winding. Transistor 130 is included to amplify the level of current being used to drive the base of transistor 132. Transistor 130 is connected between collector resistor 134 and an emitter resistor 136. The junction between the emitter of transistor 130 and its emitter resistor 136 is coupled to the base of transistor 132 through an impedance network including a resistor 138 and a parallel capacitor 140. As long as the voltage VA provided by oscillator 102 is low, transistor 130 is OFF, whereby no base current is supplied to transistor 132. Transistor 132 is, therefore, also OFF. Each pulse generated by the oscillator 102, however, turns transistor 130 ON, causing base current to be supplied to the transistor 132 through resistor 138. During the time that transistor 130 is ON, the voltage across capacitor 140 charges up to whatever voltage drop would normally occur across resistor 138 in the absence of the capacitor. The base current through transistor 132 forces transistor 132 into saturation, completing the circuit between the primary winding 94 of transformer 92 and the 30 volt supply. Current through the primary winding 94 therefore begins to increase, initially increasing at essentially a linear rate.

When the current through the primary winding 94 (as represented by the voltage drop VI across resistor 108) reaches the preset level, the pulse appearing at the base of transistor 130 is extinguished in the manner described above with respect to FIG. 2. As the base voltage at transistor 130 returns to ground level, the voltage at the emitter of the transistor similarly drops, being pulled down by the connection to ground through emitter resistor 136. The capacitor 140, however, prevents the voltage across resistor 138 from changing instantaneously, whereby the voltage at the base of transistor 132 drops by the same amount that the voltage at the emitter of transistor 130 drops. The base of transistor 132 is therefore pulled negative by several volts, substantially enhancing its capability for withstanding the inductive kick voltage which appears at its collector due to the sudden interruption of current through the primary winding 94. The voltage across the capacitor rapidly discharges through resistor 138, however, thereby returning the base of transistor 132 to ground potential prior to the next current pulse.

Each time transistor 132 is turned OFF, thereby interrupting current flow through the primary winding 94 of transformer 92, the inductance of the primary winding 94 causes the voltage VB at the collector of transistor 132 to increase to a relatively high voltage. As the voltage across the primary winding 94 increases, the voltage across the secondary winding 94 increases more rapidly, in a proportion dependent upon the ratio of turns between the two windings. The transformer 92 has a turns ratio selected so that the flyback voltage then appearing across the secondary winding 96 is in the range of between 6,000 and 8,000 volts. This voltage is rectified and filtered by a diode 150 and capacitor 152, respectively.

After the initial inductive kick, the voltage across the primary winding 94 would normally switch negative, and then oscillate back and forth between positive and negative voltages at the resonant frequency of the transformer. In the circuit of FIG. 4, however, diode 142 is connected between the collector of transistor 132 and ground in order to damp out these unwanted oscillations. When the voltage VB at collector of transistor 132 first swings negative, diode 142 becomes forward biased and begins to conduct current, thus dissipating the energy stored within the inductor. A resistor 144 and capacitor 146 are connected in series across the primary winding 94 to limit the maximum voltage and rate-of-rise of $V_B$ and thus protect transistor 132.

In the embodiment of the oscillator 102 shown in FIG. 5, a comparator 200 is the principal active element. The comparator 200 may, for example, comprise one of four identical "open collector" comparators contained within a single integrated circuit "chip", such as the "LM339N" manufactured and sold by National Semiconductor Corporation of Santa Clara, Calif. In "open collector" comparators such as the LM339N, the output terminal is the collector of a transistor whose collector is otherwise unconnected. The emitter of the transistor is connected to ground. In order to develop an output signal from an "open" collector comparators, it is necessary to connect the output of the comparator to a positive voltage source in some fashion. In the oscillator of FIG. 5, this function is performed by the resistor 210, which connects the output terminal of the comparator 200 to the +12 volt supply.

Comparator 200 has a reference voltage VR3 applied to its positive, or noninverting input. The reference voltage VR3 is principally derived from a voltage divider including resistors 204 and 206. The reference voltage VR3 is also effected by the voltage at the output of the comparator 200, however, because of a positive feedback resistor 208 connected between the output of the comparator and the noninverting input. Because of the feedback resistor 208, the reference voltage VR3 will be higher when the output of comparator 200 is high than it is when the output of comparator 200 is low.

A capacitor 212 is connected between the negative, or inverting, input of comparator 200 and ground. The inverting input of the comparator is also connected to the output of the comparator through an impedance network 214. The comparator arrangement generates the pulses for driving the high voltage flyback circuit 90 by alternately charging and discharging the capacitor 212.

As long as the voltage VE across the capacitor 212 is below the reference voltage VR3, the output transistor of comparator 200 is OFF. Thus, the output terminal of the comparator is at approximately 12 volts due to the connection with the 12 volt supply provided by resistor 210. The high signal appearing at the output of comparator 200 causes the capacitor 212 to charge through the impedance network 214, eventually reaching the reference voltage VR3. When the capacitor voltage VE reaches and surpasses the reference voltage VR3, the output transistor abruptly switches ON, forcing the voltage at the output terminal to ground potential. The switching of the output transistor causes the reference voltage VR3 to drop to a lower value, and also provides a path for capacitor 212 to discharge, again through the impedance network 214. Thus, the voltage VE will begin to diminish, eventually reaching the new, lower value of the reference VR3. At this point, the output transistor of comparator 200 will again revert to a high impedance state, causing the reference voltage to switch to its higher value and the capacitor 212 to begin recharging toward the higher reference value. The circuit will thus oscillate, producing periodic pulses at its output terminal VA.

Both the duration of the pulses and the delay between consecutive pulses are dependent upon the impedance characteristics of the impedance network 214. Impedance network 214 includes three parallel impedance legs having different conduction characteristics. First, a resistor 216 is directly connected between the output of comparator 200 and its inverting input. The resistors 216 conducts in both positive and negative directions, and therefore effects both the charging and discharging time of the capacitor 212. Second, a resistor 218 is connected in series with a diode 220 between the output of comparator 200 and its inverting input. The diode 220 is poled in such a direction that it only conducts current towards the capacitor, whereby the leg including the resistor 218 and diode 220 contributes charging current to the capacitor 212, but does not provide a path for current discharge from the capacitor 212. The third impedance leg includes resistor 222, diode 224, and a transistor switch 226. The diode 224 is poled to conduct current only away from the capacitor 212, whereby the third impedance leg conducts discharging current, but not charging current. Furthermore, the path will only conduct discharging current so long as the transistor 226 is ON. If the transistor 226 is OFF, then the third impedance leg will conduct neither charging nor discharging current, and is effectively disconnected from the circuit.

The oscillator 102 is controlled by the two control lines C1 and C2. The control line C1 is connected to the inverting input of amplifier 200 through a diode 228. The diode 228 is poled in such a direction that it can conduct charging current toward the capacitor 212, but cannot conduct discharging current away from the capacitor 212. The control line C1 is connected to the output of the current limit detector 106. As long as the output of current limit detector 106 is at a low level (at or near ground potential), the diode 228 is reversed biased and thus no current passes through the diode. During that time, the control line C1 has no impact on the operation of the circuit. Eventually the output VA of the comparator shifts to a high level, thus turning on the switch 100 and enabling current to pass through the primary winding of the flyback transformer 92. At the same time, charging current flows to the capacitor through the impedance network 214. The capacitor thus begins charging toward the reference voltage VR3. Usually, however, the voltage across the current sensing resistor 108 (FIG. 2) will reach the reference limit VR2 established by the voltage error amplifier before the capacitor voltage can charge up to VR3 on its own. When this occurs, the output of current limit detector 106 shifts to a high level. A very large amount of additional charging current is then conducted through the diode 228 to the capacitor 212, thus instantly charging it to and above the reference voltage VR3 at the noninverting input of the comparator. The output of the comparator therefore immediately switches to a low potential, disabling the switch 100 in the high voltage flyback circuit.

If a low impedance current path develops between adjacent plates of the collector stage, the high voltage generator and regulator will steadily increase the duration of pulses applied to the flyback circuit 90. Eventually, however, the oscillator will reach the maximum pulse duration established by resistors 216 and 218. Thereafter, capacitor voltage VE will reach reference voltage VR3 before control line C2 switches high, hence no further increases in pulse duration will occur. The voltage level of the high voltage signal will thus begin to diminish (causing feedback voltage VFB to similarly diminish). The level of current supplied to the plates of the air cleaner will continue to increase as high voltage drops, however, and could reach excessive levels (e.g., 100 ma) if some current-limiting mechanism were not provided. In the illustrated embodiment, the current limiting function is performed by the transistor 226 and its associated circuitry.

The control line C2 controls the state of the transistor switch 226. As stated previously, control terminal C2 of oscillator 102 is connected to the resistive divider at the output of the high voltage generator and regulator. As long as the voltage VFB is at or near the reference voltage VR1 established by the resistive divider 118, sufficient current is supplied through the resistor 230 that the transistor 226 is saturated, and is therefore fully ON. Thus, the impedance leg including the resistor 222 provides a path for discharge current from the capacitor 212, enabling the capacitor to discharge relatively rapidly. If the output of the high voltage flyback circuit drops percipitiously, however, (due, for example, to a short between adjacent plates in the collector stage 26) the feedback voltage VFB will also drop. If the voltage drops too low, the transistor 226 will turn OFF, disconnecting the third impedance leg from the circuit. This has the effect of substantially reducing the frequency of the pulses generated by the oscillator. The time delay between pulses will then be directly related to the rate at which the capacitor 212 can discharge through the resistor 216. The resistor 216 is selected such that the pulse frequency is then low enough that excessive current is not drawn by the high voltage generator and regulator circuit.

FIG. 6 illustrates one possible embodiment of the current limit detector and voltage error amplifier portions of the high voltage generator and regulator circuit of FIG. 2. The three comparators shown in the FIG. 6 circuitry represent the remaining three comparators of the LM339N integrated circuit of which the comparator 200 of FIG. 5 forms one part.

Amplifier 300 represents the voltage error amplifier 110 of FIG. 2. The negative or noninverting input of amplifier 300 is connected to the wiper arm of a potentiometer 302 which is connected between resistors 112 and 114. The potentiometer is included to permit adjustment of the feedback ratio and thus of the high voltage generated by the circuit 20. The positive or noninverting input of the comparator is connected to the junction between resistors 120 and 122, and thus receives the reference voltage VR1. A pull-up resistor 306 is connected between the output of amplifier 300 and the +12 volt supply line. A capacitor 304 is connected between the output of amplifier 300 and its inverting input to integrate and filter the error voltage appearing at the output of the amplifier. The error signal at the output of amplifier 300 is divided down by a resistive divider including resistors 308 and 310, connected in series between the output of comparator 300 and ground. The voltage VR2 at the junction between the two resistors 308 and 310 is applied to the current limit detector.

Another comparator 312 is used as the current limit detector. The voltage VI appearing across the current sensing resistor 108 is applied to the noninverting input of comparator 312, whereas the inverting input is provided with the reference voltage VR2 produced by the voltage error amplifier 110. Again, a pull-up resistor 314 is connected between the output of comparator 312 and the +12 volt supply line. The output of comparator 312 will remain low (essentially at ground potential) as long as the reference voltage VR2 exceeds the current representative voltage VI. When the current-representative voltage VI reaches and exceeds the reference voltage VR2, however, the output of comparator 312 will switch to a high level.

The circuitry illustrated in FIG. 6 also includes an indicator circuit 316. A comparator 318 is used in the indicator circuit. The comparator 318 has its noninverting input connected to the line carrying the reference voltage VR1, and its noninverting input connected to the output of comparator 300. Normally, the reference voltage VR1 will be greater than the error voltage appearing at the output of comparator 300, whereby the output of amplifier 318 will be at a low potential. The output of amplifier 318 is connected to the 30 volt source through a light emitting diode 320 and a current limiting resistor 322. As long as the output of amplifier 318 is low, the light emitting diode 320 is illuminated. The light thus indicates that the circuit is functioning properly. If the circuit ceases regulating properly, however, the output of voltage error amplifier 300 will become quite large, as the voltage at VFB drops. When the error voltage exceeds the reference voltage VR1, the output of amplifier 318 will switch high, thereby disabling the light emitting diode 320. The extinguishment of the light emitting diode 320 is an indication to the operator that the electrostatic air cleaner requires servicing.

Although the invention has been described with respect to a preferred embodiment, it will be appreciated that various rearrangements and alterations of parts may be made without departing from the spirit and scope of the present invention, as defined in the appended claims.

What is claimed is:

1. Electrostatic air cleaner apparatus for use in conjunction with space conditioning apparatus which includes a transformer for providing a low voltage AC power signal to control elements included with said space conditioning apparatus, comprising:
    power supply means adapted to be coupled to said transformer for converting said low voltage AC power signal to a low voltage DC power signal;
    high voltage generator and regulator means powered by said low voltage DC power signal for generating a high voltage DC signal suitable for energizing an electrostatic air cleaner assembly and for regulating the high voltage DC signal so that it remains within a selected range of voltages;
    an air cleaner assembly for electrostatically precipitating particles from a flow of air, said assembly including electrically conductive elements positioned in the air flow path and connected with said high voltage generator and regulator means for receiving said high voltage DC signal therefrom.

2. Apparatus as set forth in claim 1, wherein said high voltage generator and regulator means includes flyback transformer means for generating high voltage pulses in response to low voltage pulses supplied thereto, means for converting said high voltage pulses into said high voltage DC signal, and means for generating said low voltage pulses and for supplying them to said flyback transformer means.

3. Apparatus as set forth in claim 2, wherein said low voltage pulse generator means includes means for controlling the duration of said pulses in accordance with the actual magnitude of said high voltage DC signal.

4. Apparatus as set forth in claim 1, wherein said high voltage generator and regulator means includes a flyback transformer having primary and secondary windings, switch means, means for connecting said switch means in series with said primary winding across said low voltage DC power supply means, and means for periodically closing said switch means.

5. Apparatus as set forth in claim 4, wherein said means for periodically closing said switch means comprises means for generating periodic electrical pulses and for closing said switch means for the duration of each said pulse.

6. Apparatus as set forth in claim 5, wherein said switch means comprises a bipolar junction transistor having its collector-emitter current path connected in series with said primary winding and its base connected to said pulse generating means through impedance means, said impedance means comprising a parallel combination of a resistor and a capacitor, whereby each time a pulse is completed said capacitor causes said base to be reverse biased by several volts, thus enhancing its ability to withstand the inductive kick voltages generated by said primary winding.

7. Apparatus as set forth in claim 4, wherein said means for periodically closing said switch means includes means for providing a current limit reference signal, and means for causing said switch to reopen when the current through said primary winding reaches the level represented by said current limit reference signal.

8. Apparatus as set forth in claim 7, wherein said means for providing said current limit reference signal comprises means for providing a voltage reference signal representative of the desired level of said high voltage DC signal, means for providing a second signal indicative of the actual level of said high voltage, and means for integrating the difference between said voltage reference signal and said second signal so as to thereby provide an error signal, said error signal representing said current reference signal.

9. Apparatus as set forth in claim 7, wherein said means for providing said current limit reference signal comprises means for providing said current limit reference signal and for adjusting said signal in accordance with the difference between the desired and actual magnitude of said high voltage DC signal.

10. Apparatus as set forth in claim 4, and further comprising means for providing electrical pulses, means for closing said switch means for the duration of each of said pulses, means for adjusting the durations of said pulses so as to regulate the high voltage DC signal provided by said high voltage generator and regulator means, and means for reducing the frequency of said pulses if said high voltage DC signal drops below the desired level in spite of said regulation.

11. Apparatus as set forth in claim 1, wherein said power supply means comprises rectifier means for rectifying said low voltage AC power signal and capacitor means for filtering the rectified output of said rectifier means to thereby provide said low voltage DC power signal.

12. Apparatus as set forth in claim 1, and further comprising means for connecting said power supply means to said transformer, said connecting means including a sail switch or other control device capable of detecting air flow through said space conditioning apparatus, and low voltage electrical wiring for electrically connecting said sail switch or control device and power supply means to said transformer, said wiring being unprotected by conduit or armoring.

13. Electrostatic air cleaner apparatus, comprising:
power supply means for providing a low voltage DC power signal;
high voltage generator and regulator means powered by said low voltage DC power signal for generating a high voltage DC signal, said high voltage generator and regulator means including:
(a) a flyback transformer having a primary winding and a secondary winding,
(b) switch means coupled in series with the primary winding of said transformer across the low voltage DC output terminals of said power supply means,
(c) means for generating periodic pulses for controlling the state of said switch means, said switch means applying said low voltage DC signal across said primary winding for the duration of each said pulse and isolating said primary winding from said low voltage DC signal during the interval between pulses,
(d) means for causing said pulse generating means to terminate each pulse when current through said primary winding reaches a reference value,
(e) means for rectifying the high voltage signal pulses appearing across said secondary winding to thus generate said high voltage DC signal,
(f) means for adjusting said reference value in accordance with the difference between the actual and desired values of said high voltage DC signal, and
(g) means for reducing the frequency of said pulses if said high voltage DC signal drops below a selected level, less than said desired value;
an air cleaner assembly including electrically conductive elements arranged to permit air to pass around them; and
means for coupling said high voltage DC signal to elements of said air cleaner assembly.

14. Apparatus as set forth in claim 13, wherein said air cleaner assembly includes an ionizer stage and a collector stage, said ionizer stage including plural parallel corona discharge wires separated by ground plates, said collector stage including plural parallel electrically conductive plates, alternate ones of which are grounded, and wherein said high voltage DC signal is applied to the remaining, ungrounded plates of said collector stage and to said corona discharge wires.

15. Apparatus as set forth in claim 13, wherein said means for adjusting said reference value comprises first voltage divider means including plural resistors connected in series between the high voltage DC output of said high voltage generator and regulator means and ground, said first voltage divider providing a low voltage DC signal which is directly proportional to said high voltage DC signal, and means for providing a said reference value having a value equal to the integral of the difference between said low voltage DC signal provided by said first voltage divider and a second reference value.

16. Apparatus as set forth in claim 13, wherein said switch means comprises a bipolar junction transistor having its collector-emitter current path connected in series with said primary winding and its base coupled to said pulse generating means through a parallel combination of a resistor and a capacitor, whereby each time a pulse is terminated said capacitor causes said base to be reverse biased by several volts, thus enhancing the ability of the transistor to withstand the inductive kick voltages generated by said primary winding.

17. Apparatus as set forth in claim 13, wherein said power supply means is designed to be powered by a low voltage AC power signal provided by a power transformer associated with space conditioning apparatus.

18. Electrostatic air cleaner apparatus for use in conjunction with space conditioning apparatus which includes a transformer for providing a low voltage AC power signal to control elements associated with said space conditioning apparatus, comprising:
high voltage generator means adapted to be coupled to said transformer for receiving said low voltage AC power signal and responsive to said low voltage AC power signal for generating a high voltage DC signal suitable for energizing an electrostatic air cleaner assembly and for regulating the high voltage DC signal so that it remains within a selected range of voltages; and
an air cleaner assembly for electrostatically precipitating particles from a flow of air, said assembly including electrically conductive elements positioned in the air flow path and connected with said high voltage generator means for receiving said high voltage DC signal therefrom;
whereby said transformer powers both said control elements of said space conditioning apparatus and said air cleaner apparatus.

19. Apparatus as set forth in claim 18, wherein said generator means includes low voltage DC power supply means adapted to be coupled to said transformer for converting said low voltage AC power signal to a low voltage DC power signal, high voltage DC power supply means responsive to said low voltage DC power signal for generating said high voltage DC signal, and regulator means for controlling said high voltage DC power supply means so that said high voltage DC signal remains within a selected range of voltages.

20. Electrostatic air cleaner apparatus for use in conjunction with space conditioning apparatus which includes a transformer for providing a first low voltage AC power signal for powering elements of said space conditioning apparatus, comprising:

power supply means adapted to be coupled to said transformer for converting said first low voltage AC power signal to a low voltage DC power signal;

convertor means for converting said low voltage DC signal to a high voltage DC signal suitable for energizing an electrostatic air cleaner assembly, said convertor comprising oscillator means powered by said low voltage DC signal for generating a second low voltage AC signal different than said first AC signal, transformer means for converting said second AC signal into a high voltage AC signal, and rectifier means for rectifying said high voltage AC signal to provide said high voltage DC signal; and an air cleaner assembly for electrostatically precipitating particles from a flow of air, said assembly including electrically conducting elements positioned in the air flow path and connected with said converter means for receiving said high voltage DC signal therefrom.

21. Apparatus as set forth in claim 20, and further comprising means for connecting said power supply means to said transformer, said connecting means including a sail switch or other control device capable of detecting air flow through said space conditioning apparatus, and low voltage electrical wiring for electrically connecting said sail switch or control device and power supply means to said transformer, said wiring being unprotected by conduit or armoring.

* * * * *